United States Patent [19]
Mobilio et al.

[11] Patent Number: 4,578,398
[45] Date of Patent: Mar. 25, 1986

[54] SUBSTITUTED 2,3,4,9-TETRAHYDRO-1H-CARBAZOLE-1-ACETIC ACID, COMPOSITIONS AND USE

[75] Inventors: Dominick Mobilio; Christopher A. Demerson, both of Plainsboro; Leslie G. Humber, North Brunswick, all of N.J.

[73] Assignee: American Home Products Corporation, New York, N.Y.

[21] Appl. No.: 740,087

[22] Filed: May 31, 1985

[51] Int. Cl.[4] .................. A61K 31/40; C07D 209/86; C07D 209/82
[52] U.S. Cl. .................................... 514/411; 548/439
[58] Field of Search ...................... 548/439; 514/411

[56] References Cited

U.S. PATENT DOCUMENTS 3,939,178  2/1976  Demerson ..................... 260/326.28
4,057,559  11/1977  Asselin ............................. 260/315

OTHER PUBLICATIONS

Asselin et al., J. Med. Chem. 19, 787 and 792 (1976).

Primary Examiner—Robert W. Ramsuer
Attorney, Agent, or Firm—Walter Patton; John W. Routh

[57] ABSTRACT

Substituted 2,3,4,9-tetrahydro-1H-carbazole-1-acetic acid derivatives and methods for their preparation and use are disclosed. The compounds are useful analgesic and antiinflammatory agents.

8 Claims, No Drawings

SUBSTITUTED 2,3,4,9-TETRAHYDRO-1H-CARBAZOLE-1-ACETIC ACID, COMPOSITIONS AND USE

BACKGROUND OF THE INVENTION a. Field of Invention

This invention relates to tricyclic acetic acid derivatives, to their preparation and use, and to intermediates used for their preparation.

More specifically, this invention relates to tricyclic acetic acid derivatives in which the tricyclic portion thereof is characterized by having an indole portion fused to a cyclohexane ring. Still more specifically, the compounds of this invention are characterized as derivatives of the following tricyclic acetic acid system:

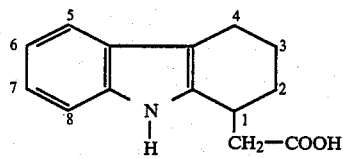

2,3,4,9-tetrahydro-1H-carbazole-1-acetic acid in which the carbons at the 1-, 4- and 8-positions are further substituted.

The tricyclic acetic acid compounds of this invention possess useful pharmacologic properties; for instance, they exhibit analgesic and antiinflammatory activity at dose levels which do not elicit undesirable side effects. The foregoing combination of attributes renders the compounds of this invention useful for the treatment of inflammatory or painful conditions in a mammal.

b. Prior Art

The closest prior art to the present invention is:

Mobilio et al. U.S. application Ser. No. 726,197 and Asselin et al. U.S. application Ser. No. 740,123. U.S. Pat. No. 4,057,559. Mobilio et al. and Asselin et al. disclose analgesic and antiinflammatory agents having the same heterocyclic ring system as the present invention but without the 1-, 4- and 8-substituents of the present invention.

Demerson et al. U.S. Pat. No. 3,939,178 discloses 1,3,4,9-tetrahydropyrano[3,4-b]indoles and 1,3,4,9-tetrahydrothiopyrano[3,4-b]indoles having analgesic and antiinflammatory activity. Related U.S. patents are U.S. Pat. Nos. 3,974,179 and 3,843,681.

Boehringer Mannheim European Patent No. 42593 generically discloses starting materials useful for producing cardiotonic and beta-blocking agents. The starting materials include 1,2,3,4-tetrahydrocarbazoles with substituents selected from the broad group including hydrogen, carboxy, lower alkyl and lower alkenyl. The starting materials are in each case also substituted with a reactive group which distinguishes them from the compounds of the present invention.

Further removed, related patents that include tetrahydrocarbazoleacetic acid derivatives useful as analgesic and antiinflammatory agents are U.S. Pat. Nos. 4,234,487; 4,264,500; 4,193,923; 4,158,007; 4,146,542; 3,896,145 and 3,824,314; Japanese Patent No. J51032556; Netherland Patent NL No. 7,100,213 and Great Britain Patent GB No. 1385620.

SUMMARY OF THE INVENTION

The compounds of this invention are represented by formula (I)

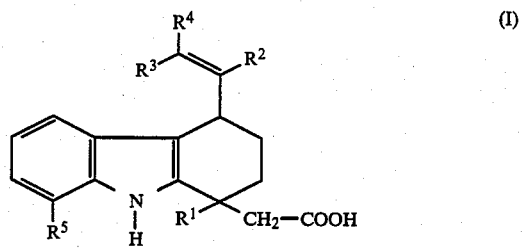

wherein $R^1$ is lower alkyl, $R^2$, $R^3$ and $R^4$ are hydrogen or lower alkyl or $R^2$ and $R^4$ are joined together to give

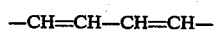

and form a benzene ring, $R^5$ is hydrogen, lower alkyl or halogen, and the pharmaceutically acceptable salts thereof.

A preferred aspect of the present invention are the compounds represented by formula (I), wherein $R^1$ is lower alkyl containing 1 to 6 carbon atoms, $R^2$, $R^3$ and $R^4$ are independently hydrogen or lower alkyl containing 1 to 6 carbon atoms or $R^2$ and $R^4$ are joined together to give

and form a benzene ring, $R^5$ is hydrogen, lower alkyl containing 1 to 6 carbon atoms or halogen, and the pharmaceutically acceptable salts thereof.

A still further preferred aspect of the present invention are the compounds represented by formula (I), wherein $R^1$ is ethyl, $R^2$, $R^3$ and $R^4$ are hydrogen or $R^2$ and $R^4$ are joined together to give

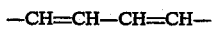

and form a benzene ring, $R^5$ is hydrogen or ethyl, and the pharmaceutically acceptable salts thereof.

The most preferred compounds of the present invention are designated 4-ethenyl-1,8-diethyl-2,3,4,9-tetrahydro-1H-carbazole-1-acetic acid, 1,8-diethyl-2,3,4,9-tetrahydro-4-phenyl-1H-carbazole-1-acetic acid and 4-(1-methylethenyl)-1,8-diethyl-2,3,4,9-tetrahydro-1H-carbazole-1-acetic acid.

The compounds of the present invention are prepared by a process in which the unsaturated ketone of structure (IV)

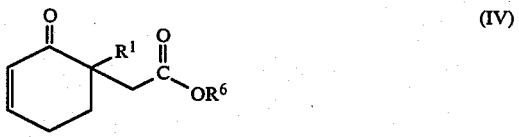

wherein $R^1$ is as defined above and $R^6$ is lower alkyl is reacted in the presence of a suitable copper catalyst selected from the group consisting of copper bromide dimethyl sulfide complex, cuprous iodide, cuprous bromide, copper acetate, cuprous chloride and tributylphosphine cuprous iodide complex, with the organometallic reagent

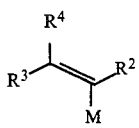

wherein $R^2$, $R^3$ and $R^4$ are as defined above and M may be MgBr, MgCl or MgI to obtain a compound of structures (V)

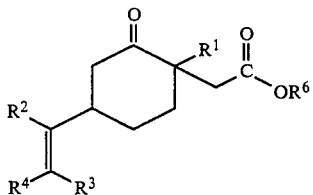

wherein $R^1$, $R^2$, $R^3$, $R^4$ and $R^6$ are as defined above and further reacting a compound of structure (V) with the substituted hydrazine of formula (VI)

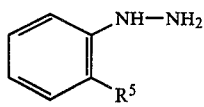

wherein $R^5$ is as defined above to obtain the corresponding hydrazone of structure (VII)

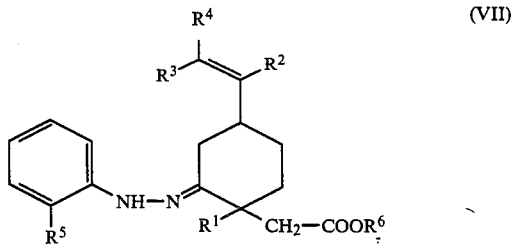

wherein $R^1$, $R^2$, $R^3$, $R^4$, $R^5$ and $R^6$ are as defined above. The hydrazone is treated with a cyclizing agent to give the ester of compound (I) and after hydrolyzing acid ester compound (I) is obtained.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "halogen" as used herein includes fluorine, chlorine, bromine and iodine.

The compounds of formula (I) form salts with suitable pharmaceutically acceptable inorganic and organic bases. These derived salts possess the same activity as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Included in the present invention are the diastereo isomers wherein the 4-substituent is either cis or trans to the acetic acid chain at position one.

Also included in this invention are the optical isomers of the compounds of formula (I) which result from asymmetric centers, contained therein. Such isomers are obtained in substantially pure form by classical separation techniques and by sterically controlled synthesis.

Antiinflammatory Activity

The useful antiinflammatory activities of the tricyclic acetic acid derivatives of formula (I) are demonstrated in standard pharmacologic tests, for example, the test designated: PREVENTATIVE ADJUVANT EDEMA.

The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access water but food is withdrawn 18 hours before testing.

Drug Preparations and Administration:

Freund's complete adjuvant is prepared by suspending 5 mg killed and dried Mycobacterium butyricum (Difco) in 1 ml liquid paraffin. The test compounds are dissolved in distilled water or suspended in distilled water with a few drops of Tween 80 according to their solubility. For primary screening all drugs are administered by gastric lavage at the arbitrary dosage of 100 mg/kg, p.o. in a volume of 0.5 ml/100 g body weight to groups of 10 animals.

Methodological Details:

The method is essentially that described by Wax et al., J. Pharmacol. Exp. Ther., 192, 166–171 (1975). Groups of rats are injected intradermally in the left hind paw with 0.1 ml of Freund's complete adjuvant. The test compound or vehicle is administered immediately before the adjuvant, 24 hours and 48 hours after the adjuvant (day 0, 1 and 2). The injected hind paw volume is measured before the injection of adjuvant and 24 hrs. after the last drug administration (day 3) by means of a plethysmometer (Buxco Electronics Inc.). The difference between the hind paw volume on day 0 and day 3 represents the edema volume. Phenylbutazone (50 mg./kg, p.o.) is included as a positive control.

Presentation of Results:

The mean edema volume (expressed as ml±SEM) is calculated for each group and the percentage protection conferred by the drug is calculated:

$$\% \text{ protection} = \frac{(c - t)100}{c}$$

where c is the mean edema volume for the untreated controls and t is the mean edema volume for the drug treated group.

A further test used to determine the utility of the compounds of the present invention is designated: DRUG EFFECTS IN PHENYLQUINONE-INDUCED WRITHING IN MICE.

The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g). The animals are fasted for 18 hours prior to use but have free access to water.

Drug Preparation and Administration:

Drugs are dissolved or suspended according to their solubility in 0.5% methyl cellulose or 0.5% Tween 80. They are administered by gastric lavage in a volume of 5 ml/kg. For primary screening all drugs are administered at the arbitrary dosage of 200 mg/kg, p.o. to a group of 10 mice.

Methodological Details:

A modification of the method of Siegmund et al., Proc. Soc. Exp. Biol. Med., 95, 729–731 (1957) is used. Groups of 5 mice are dosed with the test compound or vehicle control. Sixty minutes later the animals are injected i.p. with 0.3 ml/20 g body weight of a 0.02% solution of phenylquinone (PBQ; 2-phenyl-1,4-benzoquinone) and placed in individual observation boxes. The number of writhing or abdominal squirming movements made by each mouse during the following 15 min. period is counted. The experiment is repeated with another group of 5 mice and the mean number of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c - t)100}{c}$$

where c=mean number of writhes in the control group
where t=mean number of writhes in the test drug group Typical results obtained for the compounds of the present invention in the aforementioned tests are as follows:

| Preventative Adjuvant Edema | | |
|---|---|---|
| Compound | Dose (mg/kg, p.o.) | % Inhibition |
| Example 1 h | 25 | 62 |
| Example 1 g | 25 | 30 |
| Example 2 e | 25 | 37 |
| Example 2 d | 25 | 12 |
| Example 3 d | 50 | 25 |
| Example 3 e | 25 | 46 |

| Phenylquinone Writhing in Mice | | |
|---|---|---|
| Compound | Dose (mg/kg, p.o.) | % Inhibition |
| Example 1 h | 25 | 0 |
| Example 1 g | 25 | 21 |
| Example 2 e | 25 | 28 |
| Example 2 d | 25 | 17 |
| Example 3 d | 200 | 50 |
| Example 3 e | 25 | 0 |

The lack of side effects for the compounds of this invention are demonstrated by standard acute toxicity tests described by R. A. Turner in "Screening Methods in Pharmacology," Academic Press, New York and London, 1965, pp. 152–163 and by prolonged administration of the compound to warm-blooded animals.

When the compounds of this invention are employed as antiinflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula I of this invention will vary with the particular compound chosen and form of administration. Furthermore, it will vary with the particular host under treatment. Generally, the compounds of this invention are administered at a concentration level that affords protective effects without any deleterious side effects. These antiinflammatorily effective concentration levels are usually obtained within a therapeutic range of 1.0 µg to 500 mg/kg per day, with a preferred range of 10 µg to 100 mg/kg per day.

The compounds of this invention also possess antipyretic activity.

The compounds of this invention may be administered together with the usual doses of caffeine.

The preferred process for obtaining the compounds of the present invention is exemplified by the process for obtaining 4-substituted-1,8-diethyl-2,3,4,9-tetrahydro-1H-carbazole-1-acetic acids (XII) outlined in Scheme 1.

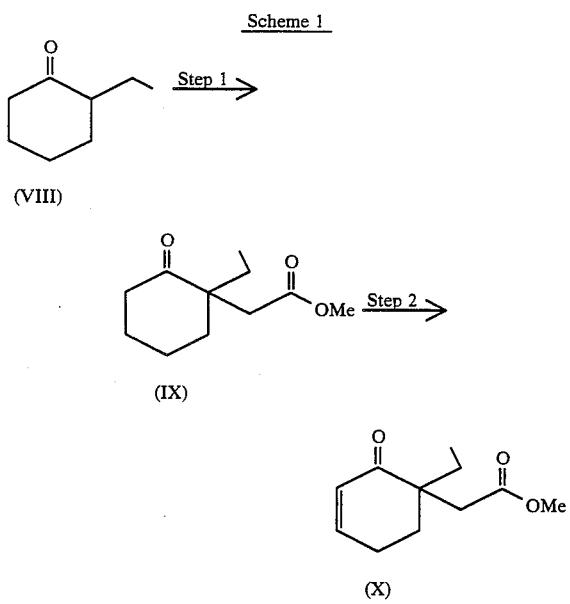

Step 1 a.KH/THF b.Et₃B c.BrCH₂COOCH₃
Step 2 a.PhSeCl/EtOAc b.H₂O₂/THF

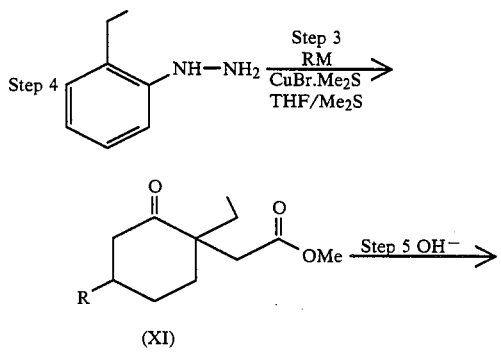

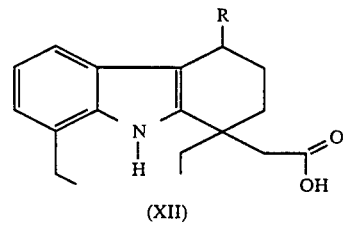

In Scheme 1, Step 1, 2-ethylcyclohexanone (VIII) was alkylated with methyl bromoacetate according to the procedure of E. Negishi et al. Tet. Lett. 24, 1341 (1983) in the presence of potassium hydride, and triethylborane in tetrahydrofuran. This afforded 2-carbomethoxymethyl-2-ethylcyclohexanone (IX) in 45% yield. Compound (IX) was previously reported in Asselin et al., J. Med. Chem., 19, 787 (1976). About 5–10% of the 2,6 regioisomer was also formed which was separated by flash chromatography.

Conversion of (IX) to 2-phenylseleno-6-carbomethoxymethyl-6-ethylcyclohexanone with phenylselenenyl chloride according to the procedure of K. B. Sharpless et al., J. Amer. Chem. Soc. 95, 6137 (1973) and oxidative elimination with hydrogen peroxide in Step 2 led to the required enone (X) in 55–68% yield in a one pot conversion.

Conjugate addition of organometallic reagents RM to (X) in Step 3 wherein R is CH=CH₂, phenyl, or C(CH₃)=CH₂ and M is MgBr gave trisubstituted ketones (XI) as a mixture of diastereomers. Fischer indole cyclization with 2-ethylphenylhydrazine in Step 4 and subsequent base hydrolysis in Step 5 gave tetrahydrocarbazoles (XII). The diastereomers, which represent another aspect of the invention, can be separated either before or after cyclization.

Conjugate addition reactions of organometallic reagents RM to (X) in Step 3 gave about a 1:1 to a 2:1 mixture of diastereomers (XI) when carried out

TABLE 1

| Entry | RM | % of Yield of (XI) | Ratio of Isomers |
|---|---|---|---|
| 1 | CH₂=CHMgBr | 69 | 56:44 |
| 2 | PhMgBr | 71 | 1:1 |
| 3 | CH₂=C(CH₃)MgBr | 71 | — | at −40° C. in tetrahydrofuran (THF) by adding an ether or THF solution of the Grignard reagent (1 to 1.4 equivalents) to a solution of (X) in THF/Me₂S containing 0.1 equivalents of copper bromide dimethyl sulfide complex [(K. J. Shea et al. Tetrahedron Lett., 24, 1003 (1983)]. See Table 1, Entry 1.

The ketones (XI) were then subjected to Fischer indole synthesis conditions in Step 4 by refluxing with 2-ethylphenylhydrazine in methanol the appropriate time to form the hydrazones (See Table 2). The hydrazone solution was then cooled to 0° C., treated with acetyl chloride to generate HCl and refluxed an additional 45 minutes to affect Fischer indole cyclization. The esters were then hydrolyzed in Step 5 with potassium carbonate in aqueous methanol to afford tetrahydro-1-H-carbazole-1-acetic acids (XII).

TABLE 2

| R | hours for hydrazone formation | % yield of ester* | % yield of (XII)* |
|---|---|---|---|
| $CH_2=CH$ | 48 | 38(26) | 65(91) |
| phenyl | 48 | 32(27) | 100(100) |
| $CH_2=C(CH_3)$ | 144 | 27(28) | 91(88) |

*The mixture of diasteromers was separated by reverse phase HPLC at the ketone (X) stage and carried on individually. The number in parenthesis refers to the yield of the second diastereomer.

The requisite starting materials of formula (VI), phenylhydrazine or substituted phenylhydrazines are known or are prepared according to known methods. A convenient method for preparing the substituted phenylhydrazines involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry," Reinhold Publishing Corporation, New York, 1961, p. 734.

The requisite starting materials of formula (IX) are prepared by several methods. At least three of these methods are illustrated in Asselin et al., U.S. Pat. No. 4,057,559.

The above starting materials of formula (V) and formula (VI) are used to prepare the compounds of this invention in the following manner:

The starting material of formula (VI) is condensed with substantially one molar equivalent of the starting material of formula (V) to give the corresponding hydrazone of formula (VII) in which $R^1$ to $R^6$ inclusive are as defined hereinbefore.

Generally speaking, the condensation is performed preferably in an inert atmosphere, for example, nitrogen or argon. Suitable solvents for the condensation include the lower alkanols such as methanol and ethanol; aromatics such as benzene and toluene; the ethers, such as tetrahydrofuran, diethyl ether, dioxane, bis(2-methoxyethyl)-ether and the like; and the halogenated hydrocarbons, methylene chloride, chloroform and the like. Methanol and ethanol are especially convenient and practical solvents. Times and temperatures for the condensation generally range from 5 minutes to five or six days at 0° to 100° C. Convenient time and temperature ranges include 20° C. to the boiling point of the mixture and 15 minutes to 130 hours.

The resulting hydrazones (VII) are then cyclized to the tricyclic ester of the acid of formula (I) by the action of a suitable cyclization agent according to the conditions of the "Fischer Indole Synthesis," for example, see B. Robinson, Chem. Rev. 63, 373 (1963).

A variety of cyclization agents are effective for this cyclization, some of the agents suitable for this cyclization include p-toluenesulfonic acid, hydrogen chloride or hydrogen chloride generated from acetyl chloride, hydrogen bromide, phosphoric acid, sulfuric acid, aluminum chloride, zinc chloride, hydrogen bromide in acetic acid, boron trifluoride-etherate, trifluoroacetic acid, cationic ion exchange resins such as Amberlite IR-120, phenyl or ethyl magnesium bromide and aniline salts. In other words the usual catalysts employed for the "Fischer Indole Synthesis" are efficacious; however, the preferred cyclization agents are hydrogen chloride or hydrogen chloride generated from acetyl chloride.

In practice the isolation of the hydrazone (VII) from the condensation reaction mixture is optional. Accordingly, the cyclization agent is added either to the above condensation reaction mixture containing the hydrazone, or to the isolated hydrazone optionally dissolved in one of the above solvents, whereby the hydrazone then cyclizes to give the corresponding tricyclic ester of formula (I) in which $R^1$ to $R^6$ inclusive are as defined hereinbefore.

The cyclization usually proceeds smoothly and rapidly. Convenient reaction times for the cyclization include five minutes to two hours, preferably 30 minutes to one hour. Convenient temperatures include 20° to 200° C., preferably 120° to 180° C.

In practice a most convenient and practical procedure for effecting the above cyclization comprises evaporating solvent from the condensation reaction mixture containing the hydrazone, and then heating the hydrazone at 120° to 200° C. in one of the aforementioned solutions of strong acids.

The starting material of formula (V) may be either a cycloalkanoneacetic acid derivative or its corresponding lower alkyl ester ($R^6$=lower alkyl). Accordingly, when the acid is employed, the above process yields the tricyclic compound identical to the desired compound of formula (I) and when the starting material is lower alkyl ester the above process yields the lower alkyl ester tricyclic compound of formula (I).

The subsequent conversion of the lower alkyl ester tricyclic compound of formula (I) to the corresponding compound of formula (I) is effected readily by subjecting the tricyclic compound to hydrolysis. Generally speaking, this conversion is most conveniently performed by employing a base as the hydrolyzing agent. The hydrolysis is performed in the presence of sufficient water optionally under an inert atmosphere, followed by acidification of the reaction mixture to yield the desired compound of formula (I). However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1967, pp. 615–617) are also applicable.

For basic hydrolysis a preferred embodiment involves subjecting the tricyclic ester to the action of a base, for example, sodium or potassium carbonate, in the presence of sufficient water to effect hydrolysis of the ester. The hydrolysis is performed using a suitable solvent, for example, methanol or ethanol under a nitrogen atmosphere.

The reaction mixture is maintained at a temperature of from 25° C. to the reflux temperature until hydrolysis occurs. Usually from 10 minutes to 48 hours is sufficient for this hydrolysis. The reaction is then rendered acidic with an acid, for example, acetic acid, hydrochloric acid, sulfuric acid and the like, to release the free acid as a solid.

Alternatively, the tricyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable solvent at a temperature of at least 60° C. and preferably from 90° C. to the boiling point of the mixture until the hydrolysis occurs. Usually from 5 to 48 hours are required for this hydrolysis. Suitable solvents include water, acetic acid, aqueous alcohols and the like. If acid hydrolysis is used, the free acid is formed directly. If necessary, the reaction mixture can be diluted with water to precipitate the product.

The following examples further illustrate this invention.

EXAMPLE 1

4-Ethenyl-1,8-diethyl-2,3,4,9-tetrahydro-1H-carbazole-1-acetic Acid (I, $R^1$=—$C_2H_5$, $R^2$=$R^3$=$R^4$=hydrogen, $R^5$=—$C_2H_5$)

(a) Preparation of 2-Ethylcyclohexanone (VIII)

2-Ethylcyclohexanol (1.6 moles, 204 g, 226 ml) was stirred in 3.2 l of acetone at 0° C. and treated with 8N Jones reagent (prepared from 106.8 g of $CrO_3$ suspended in 92 ml of concentrated sulfuric acid and diluted to 400 ml with water) until the orange color persisted (~430 ml). Isopropanol was then added to turn the solution green again after which it was poured into 2 l of ether. The product was washed with 6×500 ml of brine, dried over $MgSO_4$ and stripped of solvent. Short path distillation (b.p. 80°–85° C. at 25 mm) afforded 184 g (1.46 moles, 91%) of 2-ethylcyclohexanone as a colorless oil.

(b) Preparation of 2-Carbomethoxymethyl-2-ethylcyclohexanone (IX)

According to the procedure of E. Negishi and S. Chatterjee, Tet. Lett., 24, 1341 (1983), potassium hydride (417 mmol, 70 ml, ~6M in mineral oil) was placed under nitrogen in a three-necked flask equipped with a mechanical stirrer and was washed three times with petroleum ether (this washing can be omitted). Tetrahydrofuran (200 ml, distilled from sodium/$Ph_2CO$) was then added followed by a solution of 2-ethylcyclohexanone (VIII) (50 g, 396 mmol) in 200 ml of tetrahydrofuran added as a slow stream over ~15 minutes. The addition was followed one minute later by 495 ml of 1M $Et_3B$ in tetrahydrofuran followed 1 hour later by 594 mmol (91 g, 56 ml) of methyl bromoacetate. The yellow suspension was stirred for 2.5 hours, poured into 800 ml of water (being careful to decant away from excess KH !) and extracted with 4×300 ml of petroleum ether. The combined organic phases were dried over sodium sulfate and concentrated in vacuo. The product was distilled through a 6 inches Vigreux column collecting the material boiling at 107°–118° C. at 0.8 mm (the two regioisomers from the alkylation). This material was then purified by flash chromatography to afford 35.33 g (178.2 mmol, 45%) of colorless oil. The desired product is the lower $R_f$ material of the two overlapping spots on thin layer. $R_f$=0.23 in 10% ethyl acetate/petroleum ether. About 5-10% of the 2,6 regioisomer can be isolated as the top spot.

(c) Preparation of 6-Carbomethoxymethyl-6-ethyl-2-cyclohexen-1-one (X)

The ketone, 2-carbomethoxymethyl-2-ethylcyclohexanone (IX) (141 mmol, 28 g) was stirred in 1.25 l of ethyl acetate (dried over 3A molecular sieves) and treated with 169 mmol (32.5 g) of PhSeCl. The reaction was stirred under nitrogen for 4 hours then treated with 250 ml of water. The mixture was shaken vigorously in a separatory funnel and the organic phase was returned to the reaction flask. Tetrahydrofuran (550 ml) was then added followed by 35 ml of 30% $H_2O_2$ (aq.) added dropwise. The reaction mixture was stirred for one hour then washed with 500 ml of water and 500 ml of saturated $Na_2CO_3$ (aq.). The product was then dried over $MgSO_4$ and concentrated in vacuo. Flash chromatography afforded 15.3 g (78.0 mmol, 55%) of the product as a pale yellow oil. $R_f$=0.9 in 15% ethyl acetate/petroleum ether on TLC.

(d) Preparation of 2-Carbomethoxymethyl-5-ethenyl-2-ethylcyclohexanone (XI, R=—CH=$CH_2$)

The enone, 6-carbomethoxymethyl-6-ethyl-2-cyclohexen-1-one, prepared by the process of Step (c) (58.1 mmol, 11.4 g), 5.81 mmol (1.194 g) of $CuBr.Me_2S$ and 11.7 ml of $Me_2S$ were stirred in 176 ml of THF at $-40°$ C. under nitrogen and treated with 58.1 mmol (58.1 ml of 1M solution in THF) of vinylmagnesium bromide added dropwise over 45 minutes. The reaction was then quenched with 200 ml of 1M HCl (aq.) and extracted with 5×100 ml of petroleum ether. Drying ($MgSO_4$) and flash chromatography afforded 8.96 g (39.9 mmol, 69% pale yellow oil) of product as a mixture of diastereomers. The diastereomers (56:44 ratio) were separated by preparative HPLC on a Prep 500A using a brand of silica gel available from Waters Associates, Milford, Ma., and designated "more polar isomer" and "less polar isomer."

| NMR-60 $MH_z$ (more polar isomer): | | |
|---|---|---|
| No. of Protons | Type | Chemical Shift/Splitting |
| 3 | $CH_2\underline{CH_3}$ | 0.85/t J=7 |
| 9 | $CH_2$ and CH | 1.2–2.3/m |
| 2 | $CH_2COOMe$ | 2.65/broad s |
| 3 | $OCH_3$ | 3.62/s |
| 3 | \>C=CH$_2$ (vinyl) | 4.8–6.3/m |

| NMR-60 $MH_z$ (less polar isomer) | | |
|---|---|---|
| No. of Protons | Type | Chemical Shift/Splitting |
| 3 | $CH_2\underline{CH_3}$ | 0.55/t J=7 |
| 11 | $CH_2$ and CH | 1.0–2.7/m |
| 3 | $OCH_3$ | 3.45/s |
| 2 | =CH$_2$ | 4.5–4.9/m |
| 1 | \>C=CH— | 5.2–5.85/m |

(e) Preparation of 4-Ethenyl-1,8-diethyl-2,3,4,9-tetrahydro-1H-carbazole-1-acetic Acid Methyl Ester The more polar ketone isomer of 2-carbomethoxymethyl-5-ethenyl-2-ethylcyclohexanone (5.084 g, 22.66 mmol) and the 2-ethylphenylhydrazine (3.086 g, 22.66 mmol) were heated at reflux in 97 ml of methanol under nitrogen for 48 hours. The reaction was then cooled to 0° C., treated with 45.32 mmol (3.56 g, 3.22 ml) of AcCl and refluxed an additional 45 minutes. Cooling, concentration and flash chromatography afforded 2.772 g (8.52 mmol, 38%) of indole as an orange oil. $R_f$=0.47 in 15% ethyl acetate/petroleum ether on TLC.

| | NMR-60 MH$_z$: | |
|---|---|---|
| No. of Protons | Type | Chemical Shift/Splitting |
| 3 | CH$_2$C$\underline{H}_3$ | 0.85/t J=7 |
| 3 | ArCH$_2$C$\underline{H}_3$ | 1.4/t J=8 |
| 6 | CH$_2$ | 1.55-2.2/m |
| 4 | CH$_2$ | 2.45-3.15/m |
| 3 | OCH$_3$ | 3.7/s |
| 1 | C$\underline{H}$CH=CH$_2$ | 3.7/m |
| 1 | HC=CH$_2$ (H cis) | 5.0/m |
| 1 | HC=CH$_2$ (H trans) | 5.2/m |
| 1 | H$\underline{C}$=CH$_2$ | 5.6-6.35/m |
| 3 | aromatic | 6.9-7.5/m |
| 1 | NH | 9.45/broad s |

(f) The less polar ketone isomer was taken on to the indole in the same way to provide the product with the following NMR spectrum:

NMR (CDCl$_3$/TMS, 60 MH$_z$): 0.85 (t, 3H, J=7, CH$_2$C$\underline{H}_3$), 1.35 (t, 3H, J=7, ArCH$_2$C$\underline{H}_3$), 1.65-2.2 (m, 6H, C$\underline{H}_2$), 2.55-3.0 (m, 4H, CH$_2$), 3.67 (m, 1H, C$\underline{H}$CH=CH$_2$), 3.67 (s, 3H, OCH$_3$), 4.95-6.3 (m, 3H, C$\underline{H}$=C$\underline{H}_2$), 7.0-7.35 (m, 3H, aromatics), 9.3 (broad s, 1H, NH).

(g) Preparation of 4-Ethenyl-1,8-diethyl-2,3,4,9-tetrahydro-1H-carbazole-1-acetic Acid (XII, R=—CH=CH$_2$)

The ester (8.44 mmol, 2.7467 g, from the polar ketone, prepared in Step (e), was refluxed in 76 ml of 8:1 v:v methanol/water containing 9.115 mmol (1.260 g) of K$_2$CO$_3$. After 24 hours approximately 200 mg of K$_2$CO$_3$ were added and the reaction was refluxed another 24 hours. At this point most of the solvent was removed in vacuo, the residue was dissolved in 20 ml of water and it was acidified to pH=1 with ~5 ml of 3M HCl (aq.). The product was extracted with 4×25 ml of ether, dried over magnesium sulfate and concentrated. Flash chromatography afforded 1.71 g (5.49 mmol) of orange oil. The product was crystallized from 10 ml of 2.5:1 petroleum ether (30-60)/benzene to afford 920 mg (35% yield) of beige cubes which were dried in vacuo (78° C., silica gel) for 8 hours, m.p. 144°-147° C.

| | NMR-60 MH$_z$: | |
|---|---|---|
| No. of Protons | Type | Chemical Shift/Splitting |
| 3 | CH$_2$C$\underline{H}_3$ | 0.9/t J=7 |
| 3 | ArCH$_2$C$\underline{H}_3$ | 1.35/t J=7 |
| 6 | CH$_2$ | 1.7-2.3/m |
| 2 | ArC$\underline{H}_2$CH$_3$ | 2.85/q J=7 |
| 2 | C$\underline{H}_2$COOH | 2.75/s |
| 1 | C$\underline{H}$C=C | 3.65/m |
| 1 | =C(H)- | 5.0/m |
| 1 | =CH- | 5.2/d of d |
| 1 | H$_2$C=C$\underline{H}$- | 5.7-6.3/m |
| 3 | aromatic | 7.0-7.6 |
| 1 | OH | 7.9/broad m |
| 1 | NH | 8.9/broad m |

IR (KBr): 3490(OH), 3420(NH), 1715(C=O).

(h) The ester (4.078 mmol, 1.3272 g, derived from the less polar ketone, prepared in Step (f)), and K$_2$CO$_3$ (4.404 mmol, 609 mg) were heated at reflux in 37 ml of 8:1 (v:v) MeOH/H$_2$O for 24 hours. Another 200 mg of K$_2$CO$_3$ were then added and the reaction was refluxed an additional 24 hours. Most of the MeOH was then removed in vacuo and the residue was dissolved in 20 ml of water and acidified to pH ~1 with ~5 ml of 3M HCl (aq.). The product was extracted with 4×25 ml of petroleum ether, dried over MgSO$_4$ and concentrated. Flash chromatography afforded 1.15 g (3.702 mmol, 91%) of brown oil. The compound was triturated with petroleum ether to give 380 mg of tan crystals which were dried at 78° C. for 8 hours, m.p. 98°-103° C.

NMR (CDCl$_3$/TMS, 60 MH$_z$): 0.9 (t, 3H, J=7, CH$_2$C$\underline{H}_3$), 1.4 (t,3H, J=7, ArCH$_2$C$\underline{H}_3$), 1.7-2.3 (m, 6H, CH$_2$), 2.9 (q, J=7, 2H, ArC$\underline{H}_2$CH$_3$), 2.7 (s, 2H, C$\underline{H}_2$COOH), 3.6 (m, 1H, CHC=C), 4.8-5.2 (m, 2H, C=CH$_2$), 6.0 (m, 1H, C$\underline{H}$=CH$_2$), 6.8-7.5 (m, 3H, aromatics), 8.9 (broad s, 2H, NH and OH).

IR (KBr): 2300-3700(OH), 3400(NH), 1700(C=O), 1640 and 1610(C=C).

EXAMPLE 2

1,8-Diethyl-2,3,4,9-tetrahydro-4-phenyl-1H-carbazole-1-acetic acid (I, R$^1$=R$^5$=—C$_2$H$_5$, R$^3$=hydrogen, R$^2$ and R$^4$ joined to form —CH=CH—CH=CH—)

(a) Preparation of 2-Carbomethoxymethyl-2-ethyl-5-phenylcyclohexanone (XI, R=phenyl)

The enone, 6-carbomethoxymethyl-6-ethyl-2-cyclohexen-1-one (X) prepared by the process of Example 1, Step (c) (61.1 mmol, 12.0 g), CuBr.Me$_2$S (6.11 mmol, 1.256 g) and Me$_2$S (12.3 ml) were stirred in 85 ml of dry THF at −40° C. under nitrogen and treated with 61.1 mmol (20.4 ml of 3M in THF), of PhMgBr added dropwise over 30 minutes. The reaction was then quenched with 250 ml of 1M HCl (aq.) and extracted with 4×100 ml of petroleum ether. Drying (Na$_2$SO$_4$) and flash chromatography afforded 11.87 g (43.3 mmol, 71%) of product. The two diastereomers were separated by preparative HPLC on a Prep 500A using a brand of silica gel available from Waters Associates, Milford, Ma., affording 4.8 g of each isomer, designated "less polar isomer" and "more polar isomer."

| | NMR-60 MH$_z$ (less polar isomer): | |
|---|---|---|
| No. of Protons | Type | Chemical Shift/Splitting |
| 3 | CH$_2$C$\underline{H}_3$ | 0.85/t J = 7 |
| 8 | CH$_2$ | 1.55-2.25/m |
| 2 | C$\underline{H}_2$COOMe CH$_2$C=O | 2.5-2.7/m |
| 3 | OCH$_3$ | 3.7/s |
| 1 | ArCH | 3.0/m |

-continued

NMR-60 MH$_z$ (less polar isomer):

| No. of Protons | Type | Chemical Shift/Splitting |
|---|---|---|
| 5 | aromatic | 7.35/s |

IR (less polar isomer): 1745, 1715 C=O.

NMR-60 MH$_z$ (more polar isomer)

| No. of Protons | Type | Chemical Shift/Splitting |
|---|---|---|
| 3 | CH$_2$CH$_3$ | 0.85/t J = 7 |
| 6 | ring CH$_2$ | 1.5–2.3/m |
| 4 | CH$_2$COOMe CH$_2$C=O | 2.6–2.8/m |
| 1 | ArCH | 3.1/m |
| 3 | OCH$_3$ | 3.64/s |
| 5 | aromatics | 7.32/s |

(b) Preparation of 1,8-Diethyl-2,3,4,9-tetrahydro-4-phenyl-1H-carbazole-1-acetic Acid Methyl Ester The ketone (more polar isomer prepared in Step (a), 16.25 mmol, 4.458 g) and 2-ethylphenylhydrazine (16.25 mmol, 2.213 g) were refluxed in 70 ml of methanol under nitrogen for 48 hours. The reaction was cooled to 0° C., treated with 32.5 mmol (2.55 g, 2.3 ml) of AcCl and refluxed an additional hour. The solution was then concentrated in vacuo and purified by flash chromatography to afford 1.92 g (5.23 mmol, 32%) of yellow oil.

NMR-60 MH$_z$:

| No. of Protons | Type | Chemical Shift/Splitting |
|---|---|---|
| 3 | CH$_2$CH$_3$ | 0.8/t, J = 7 |
| 3 | ArCH$_2$CH$_3$ | 1.4/t, J = 7 |
| 6 | ring CH$_2$ CH$_2$CH$_3$ | 1.5–2.1/m |
| 2 | CH$_2$COOMe | 2.65/broad s |
| 2 | ArCH$_2$CH$_3$ | 2.85/q, J = 7 |
| 3 | OCH$_3$ | 3.57/s |
| 1 | PhCH | 4.1/broad t, J = 7 |
| 3 | aromatic | 6.65–6.45/m |
| 5 | Ph | 7.2/s |
| 1 | NH | 9.3/broad s |

IR: NH 3390 C=O 1730.

(c) The less polar ketone isomer was taken on to the indole in the same manner to provide the product with the following NMR spectrum:

NMR (CDCl$_3$/TMS, 60 MH$_z$): 0.85 (t, J=7, 3H, CH$_2$CH$_3$), 1.35 (t, J=7, 3H, ArCH$_2$CH$_3$), 1.55–2.25 (m, 6H, ring CH$_2$ and CH$_2$CH$_3$), 2.7 (broad s, 2H, CH$_2$COOMe), 2.85 (q, J=7, 2H, ArCH$_2$CH$_3$), 3.7 (s, 3H, OCH$_3$), 4.2 (broad t, 1H, PhCH), 6.7–7.0 (M, 3H, indole aromatics), 7.25 (s, 5H, Ph), 9.5 (broad s, 1H, NH).

(d) Preparation of 1,8-Diethyl-2,3,4,9-tetrahydro-4-phenyl-1H-carbazole-1-acetic Acid (XII, R=phenyl)

The ester (1.964 g, 5.23 mmol), prepared in Step (b), derived from the more polar ketone, and K$_2$CO$_3$ (6.28 mmol, 867 mg) were refluxed under nitrogen in 42 ml of MeOH containing 5.2 ml of water. After 24 hours at reflux and 16 hours at room temperature (the reaction was done by TLC after the reflux) most of the methanol was removed in vacuo and the residue was dissolved in 20 ml of water. It was acidified to pH~1 with 3M HCl (aq.) and extracted with 4×25 ml of ether. Drying (MgSO$_4$) and flash chromatography afforded 1.89 g (5.23 mmol, 100%) of orange oil which was crystallized from 10 ml of 2:1 petroleum ether/benzene. Collected were 1.2 g of off-white powder which were shown by elemental analysis and NMR to be a 1:1 complex with benzene. Drying in vacuo at 78° C. (silica gel desiccant) removed the benzene, m.p. 140°–142.5° C.

NMR (CDCl$_3$/TMS, 60 MH$_z$): 0.9 (t, J=7, 3H, CH$_2$CH$_3$), 1.34 (t, J=7, 3H, ArCH$_2$CH$_3$), 1.6–2.6 (m, 6H, ring CH$_2$ and aliphatic CH$_2$CH$_3$), 2.9 (s, 2H, CH$_2$COO), 2.9 (q, J=7, ArCH$_2$CH$_3$), 4.2 (m, 1H, PhCH), 6.7–7.0 (m, 3H, indole aromatics), 7.3 (s, 5H, Ph), 8.9 (broad s, 1H, NH).

IR (KBr): 3480(NH), 3600–2500(OH), 3100–2800(CH), 1710(C=O).

(e) The ester, (4.62 mmol, 1.7342 g), prepared in Step (c), derived from the less polar ketone, and K$_2$CO$_3$ (5.54 mmol, 766 mg) were refluxed under nitrogen in 37 ml of MeOH containing 4.63 ml of water. After 24 hours at reflux and 16 hours at room temperature, most of the methanol was removed in vacuo and the residue was dissolved in 20 ml of water. The solution was acidified to pH~1 with 3M HCl (aq.) and extracted with 4×25 ml of ether. Drying (MgSO$_4$) and flash chromatography afforded 1.69 g (4.68 mmol, 100%) of orange oil. About 1.5 g were recrystallized from 10 ml of 2:1 petroleum ether/benzene. The product formed as a solid mass which was ground into a pale yellow powder and washed with petroleum ether. Drying at 78° C. in vacuo (silica gel desiccant) gave 850 mg of pure product, m.p. 118°–121° C.

NMR (CDCl$_3$/TMS): 0.93 (t, J=7, 3H, CH$_2$CH$_3$), 1.37 (t, J=7, 3H, ArCH$_2$CH$_3$), 1.6–2.5 (M, 6H, ring CH$_2$ and aliphatic CH$_2$CH$_3$), 2.8 (s, 2H, CH$_2$COO), 2.9 (q, J=7, 2H, ArCH$_2$CH$_3$), 4.28 (m, 1H, PhCH), 6.9 (m, 3H, indole aromatics), 7.25 (s, 5H, Ph), 9.1 (broad s, 1H, NH).

IR (KBr): 3450(NH), 3600–3100(OH), 1710(C=O).

EXAMPLE 3

4-(1-Methylethenyl)-1,8-diethyl-2,3,4,9-tetrahydro-1H-carbazole-1-acetic Acid (I, $R^1=R^5=$—C$_2$H$_5$, $R^2=$—CH$_3$, $R^3=$hydrogen)

(a) Preparation of 2-Carbomethoxymethyl-2-ethyl-5-(1-methylethenyl)-cyclohexanone (XI, R=—C(CH$_3$)=CH$_2$)

The enone, 6-carbomethoxymethyl-6-ethyl-2-cyclohexene-1-one, (X), prepared in Example 1, Step (c), (33.12 mmol, 6.50 g), CuBr.Me$_2$S (3.312 mmol, 681 mg) and Me$_2$S (6.63 ml) were stirred in 97.5 ml of dry THF at −40° C. under nitrogen and treated with 49.68 mmol (66.24 ml of 0.75M in THF, prepared from treating isopropenyl bromide with 1.1 equivalents of Mg) of isopropenylmagnesium bromide added dropwise. The reaction was quenched with 120 ml of 1M HCl (aq.) and extracted with 4×60 ml of petroleum ether. Drying (Na$_2$SO$_4$) and flash chromatography afforded 5.6 g (23.53 mmol, 71%) of colorless oil as a mixture of diastereomers. The diastereomers were separted by preparative HPLC on a Prep 500A using a brand of silica gel available from Waters Associaes, Milford, Ma., to provide a "less polar isomer" and a "more polar isomer."

Less polar isomer:

NMR (CDCl$_3$/TMS, 200 MH$_z$): 0.724 (t, J=7.3, 3H, CH$_2$CH$_3$), 1.2–2.2 (m, 6H, CCH$_2$CH$_2$C, CH$_2$CH$_3$), 1.676 (s, 3H, C=CHCH$_3$), 2.3–2.9 (m, 5H, CH$_2$C=O, CH$_2$COO, C=CCH$_3$CH), 3.584 (s, 3H, OCH$_3$), 4.6–4.7 (m, 2H, C=CH$_2$).

IR (neat): 3100 (CH vinyl and aromatic), 3000–2900 (CH aliphatic), 1745 (COOMe), 1715 (C=O).

More polar isomer:

NMR (CDCl$_3$/TMS, 200 MH$_z$): 0.843 (t, J=7.3, 3H, CH$_2$CH$_3$), 1.2–2.2 (m, 6H, CCH$_2$CH$_2$C, CH$_2$CH$_3$), 1.743 (s, 3H, C=CHCH$_3$), 2.3–2.9 (m, 5H, CH$_2$C=O, CH$_2$COO, C=CCH$_3$CH), 3.626 (s, 3H, OCH$_3$), 4.75 (M, 2H, C=CH$_2$).

IR (neat): 3100 (CH vinyl and aromatic), 3000–2900 (CH aliphatic), 1745 (COOMe), 1715 (C=O).

(b) Preparation of 4-(1-Methylethenyl)-1,8-diethyl-2,3,4,9-tetrahydro-1H-carbazole-1-acetic Acid Methyl Ester The less polar ketone isomer prepared in Step (a), (18.61 mmol, 4.43 g) and 2-ethylphenylhydrazine (24.2 mmol, 3.3 g) were refluxed in 80 ml of MeOH under nitrogen for 144 hours. The reaction mixture was cooled to 0° C., treated with 37.2 mmol (2.92 g, 2.65 ml) of AcCl and refluxed an additonal 45 minutes. Concentration in vacuo and flash chromatography afforded 1.73 g (5.10 mmol, 27%) of orange oil.

Carbazole derived from the less polar ketone:

NMR (CDCl$_3$/TMS, 200 MH$_z$): 0.857 (t, 3H, J=7.61, CH$_2$CH$_3$), 1.376 (t, 3H, J=7.61, ArCH$_2$CH$_3$), 1.6–2.3 (m, 6H, CHCH$_2$CH$_2$C, CH$_2$CH$_3$ aliphatic), 1.760 (s, 3H, C=CCH$_3$), 2.6–2.9 (m, 4H, CH$_2$COO, ArCH$_2$CH$_3$), 3.67 (m, 1H, C=CCH$_3$CH), 3.702 (s, 3H, OCH$_3$), 4.689 (s, 1H, C=CH$_2$), 4.863 (s, 1H, C=CH$_2$), 6.95–7.5 (m, 3H, aromatics), 9.42 (broad s, 1H, NH).

IR (neat): 3410(NH), 3100(vinyl CH), 3000–2900(CH), 1740(C=O).

(c) The more polar ketone isomer prepared in Step (a) was treated in the same manner to afford 1.71 g (5.04 mmol, 28%) of carbazole:

Carbazole derived from the more polar ketone:

NMR (CDCl$_3$/TMS, 200 MH$_z$): 0.849 (t, 3H, J=7.62, CH$_2$CH$_3$), 1.379 (t, 3H, J=7.62, ArCH$_2$CH$_3$), 1.6–2.3 (m, 6H, CCH$_2$CH$_2$C, CCH$_2$CH$_3$ aliphatic), 1.731 (s, 3H, C=C CH$_3$), 2.682 (s, 2H, CH$_2$COO), 2.873 (q, 2H, J=7.6, ArCH$_2$CH$_3$), 3.6 (m. 1H, H$_2$C=CH$_3$CH), 3.681 (s, 3H, OCH$_3$), 4.73 (s, 1H, C=CH$_2$), 4.87 (s, 1H, C=CH$_2$), 6.95–7.5 (m, 3H, aromatics), 9.2 (broad s, 1H, NH).

IR (neat): 3410(NH), 3100(vinyl CH), 3000–2900(CH), 1740(C=O).

(d) Preparation of 4-(1-Methylethenyl)-1,8-diethyl-2,3,4,9-tetrahydro-1H-carbazole-1-acetic Acid (XII, R=—C(CH$_3$)=CH$_2$)

The 4-(1-methylethenyl)-1,8-diethyl-2,3,4,9-tetrahydro-1H-carbazole-1-acetic acid methyl ester (1.72 g, 5.08 mmol), prepared in Step (b), derived from the less polar ketone, and 7.11 mmol of K$_2$CO$_3$ (0.983 g) were refluxed under nitrogen in 40.6 ml of MeOH containing 5.1 ml of water. After 24 hours, most of the methanol was removed in vacuo and the residue was dissolved in 15 ml of water. It was acidified to pH~1 with 3M HCl (aq.) and extracted with 4×40 ml of ether. Drying (MgSO$_4$) and flash chromatography afforded 1.51 g (4.65 mmol, 91%) of yellow oil. The compound was recrystallized from 2:1 petroleum ether/benzene to give 988 mg of white powder which was dried at 78° C. (high vacuum, phosphorous pentoxide) m.p. 133.5°–135° C.

NMR (CDCl$_3$/TMS, 200 MH$_z$): 0.883 (t, 3H, J=7.62, CH$_2$CH$_3$), 1.346 (t, 3H, J=7.62, ArCH$_2$CH$_3$), 1.6 (m, 1H) and 1.9–2.1 (m, 5H, CCH$_2$CH$_2$C, CH$_2$CH$_3$), 1.778 (s, 3H C=CCH$_3$), 2.75 (ABq, 2H, CH$_2$COO), 2.841 (q, 2H, J=7.62, ArCH$_2$CH$_3$), 3.587 (broad t, 1H C=CCH$_3$CH), 4.648 and 4.867 (2s, 2H, C=CH$_2$), 7.0–7.41 (m, 3H, aromatics), 8.965 (broad s, 1H, NH).

IR (KBr): 3445(NH), 3500–3000(OH), 3070(vinyl H and aryl H), 3000–2840(CH), 1708(C=O).

Analysis: Calculated: C(77.49%), H(8.37%), N(4.31%). Found: C(77.62%), H(8.31%), N(4.27%).

(e) The 4-(1-methylethenyl)-1,8-diethyl-2,3,4,9-tetrahydro-1H-carbazole-1-acetic acid methyl ester (1.71 g, 5.04 mmol), prepared in Step (c), derived from the more polar ketone, and 7.06 mmol of K$_2$CO$_3$ (0.975 g) were refluxed under nitrogen in 40.3 ml of MeOH containing 5 ml of water. After 24 hours, most of the methanol was removed in vacuo and the residue was dissolved in 15 ml of water. It was acidified to pH~1 with 3M HCl (aq.) and extracted with 4×40 ml of ether. Drying (MgSO$_4$) and flash chromatography afforded 1.45 g (4.46 mmol, 88%) of yellow oil. The compound was recrystallized from 2:1 petroleum ether/benzene to afford 1.11 g of white powder which was dried at 78° C. (high vacuum, phosphorus pentoxide) m.p. 117.5°–119° C.

NMR (CDCl$_3$/TMS, 200 MH$_z$): 0.875 (t, 3H, J=7.62, CH$_2$CH$_3$), 1.338 (t, 3H, J=7.62, ArCH$_2$CH$_3$), 1.725 (s, 3H, C=CCH$_3$), 1.8–2.2 (m, 6H, CH$_2$CH$_3$, CCH$_2$CH$_2$C), 2.762 (s, 2H, CH$_2$COO), 2.827 (q, 2H, J=7.62, ArCH$_2$CH$_3$), 3.607 (broad t, 1H, C=CCH$_3$CH), 4.774 and 4.883 (2S, 2H, H$_2$C=C), 7.0–7.5 (m, 3H, aromatics), 8.755 (broad s, 1H, NH).

IR (KBr): 3340(NH), 3500–3000(OH), 3050(vinyl H and aryl H), 3000–2800(CH), 1700(C=O).

Analysis: Calculated: C(77.49%), H(8.37%), N(4.31%). Found: C(77.65%), H(8.27%), N(4.25).

We claim:

1. A compound of the formula (I)

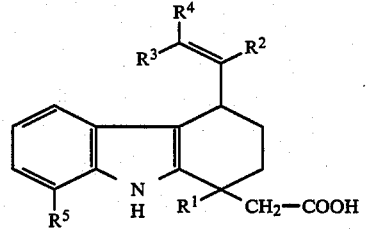

wherein R$^1$ is lower alkyl, R$^2$, R$^3$ and R$^4$ are hydrogen or lower alkyl or R$^2$ and R$^4$ are joined together to give

—CH=CH—CH=CH— and form a benzene ring, R$^5$ is hydrogen, lower alkyl or halogen, and the pharmaceutically acceptable salts thereof.

2. A compound according to claim 1 wherein R$^1$ is lower alkyl containing 1 to 6 carbon atoms, R$^2$, R$^3$ and R$^4$ are independently hydrogen or lower alkyl containing 1 to 6 carbon atoms or R$^2$ and R$^4$ are joined together to give

—CH=CH—CH=CH— and form a benzene ring, R$^5$ is hydrogen, lower alkyl containing 1 to 6 carbon atoms or halogen, and the pharmaceutically acceptable salts thereof.

3. A compound according to claim 2 wherein R$^1$ is ethyl, R$^2$, R$^3$ and R$^4$ are hydrogen or R$^2$ and R$^4$ are joined together to give

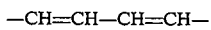

and form a benzene ring, $R^5$ is hydrogen or ethyl, and the pharmaceutically acceptable salts thereof.

4. A compound according to claim 3 designated 4-ethenyl-1,8-diethyl-2,3,4,9-tetrahydro-1H-carbazole-1-acetic acid.

5. A compound according to claim 3 designated 4-(1-methylethenyl)-1,8-diethyl-2,3,4,9-tetrahydro-1H-carbazole-1-acetic acid.

6. A compound according to claim 3 designated 1,8-diethyl-2,3,4,9-tetrahydro-4-phenyl-1H-carbazole-1-acetic acid.

7. A pharmaceutical composition comprising a compound of structure (I), or a pharmaceutically acceptable salt thereof, as defined in claim 1 and a pharmaceutically acceptable carrier.

8. A method for treating inflammatory or painful conditions in a mammal which comprises the administration to said mammal of an effective amount of a compound selected from those of formula (I), or a pharmaceutically acceptable salt thereof, as defined in claim 1.

* * * * *